United States Patent [19]
Alcoz

[11] Patent Number: 5,894,531
[45] Date of Patent: Apr. 13, 1999

US005894531A

[54] METHOD AND APPARATUS FOR DETECTION OF ULTRASOUND USING A FIBER-OPTIC INTERFEROMETER

[75] Inventor: Jorge J. Alcoz, San Antonio, Tex.

[73] Assignee: Karta Technology, Inc., San Antonio, Tex.

[21] Appl. No.: 08/814,841

[22] Filed: Mar. 11, 1997

[51] Int. Cl.$^6$ ..................................... G02B 6/27
[52] U.S. Cl. ..................... 385/11; 250/227.27; 356/351; 385/15
[58] Field of Search .................. 385/11–13, 15, 385/24, 27, 28; 356/345, 349–351, 358, 357, 364, 365; 250/227.17, 227.19, 227.27

[56] References Cited

U.S. PATENT DOCUMENTS

| | | | |
|---|---|---|---|
| 3,630,622 | 12/1971 | Delft et al. | 356/365 |
| 4,572,949 | 2/1986 | Bowers et al. | 250/227.27 |
| 4,881,817 | 11/1989 | Kim et al. | 356/350 |
| 4,966,459 | 10/1990 | Monchalin | 356/358 |
| 5,120,130 | 6/1992 | Bergh | 356/350 |
| 5,285,257 | 2/1994 | Negishi et al. | 356/350 |
| 5,680,212 | 10/1997 | Blouin et al. | 356/357 |

OTHER PUBLICATIONS

"Nondestructive Evaluation with laser ultrasound," Mechanical Engineering, 1994, p. 63, vol. 116, (Oct.).

J.P. Monchalin, "Optical detection of ultrasound," IEEE Transactions on Ultrasonics, Ferroelectrics, and Frequency Control, Sep. 1986, p. 485, vol. UFFC–33, No. 5.

J.W. Wagner, "Breaking the sensitivity barrier: the challenge for laser–ultrasonics," IEEE Ultrasonics Symposium, 1992, p. 791, 1051–0117/92, [no month].

M.J. Messerly, R.C. Mikkelson and J.R. Onstott, "A broadband single polarization optical fiber," Journal of Lightwave Technology, Jul. 1991, vol. 9, No. 7, p. 817.

J.V. Delden, "New 3–port/4–port optical circulator," Photonics Spectra, Jan. 1992, p. 81.

Primary Examiner—John D. Lee
Attorney, Agent, or Firm—Gustav N. Van Steenberg

[57] ABSTRACT

A method and apparatus for detection of ultrasonic vibrations using an interferometer built, in its preferred embodiment, with optical fibers is disclosed. The method and apparatus are particularly useful where perturbations and disturbances adversely affecting other interferometer configurations are encountered. Light from a laser is split into two orthogonal polarization modes which travel through different fiber-optic paths and are directed to the object being investigated. A waveplate and a polarization splitter are used to re-direct the reflected light into the optical path opposite from which it arrived. A second polarization splitter combines the returning light and an interference signal is obtained with photodetectors. The bias phase-shift between the interfering beams is fixed with a second waveplate. The detected signal is the result of motion which modulates the phase of the light reflected by the object being inspected.

20 Claims, 6 Drawing Sheets

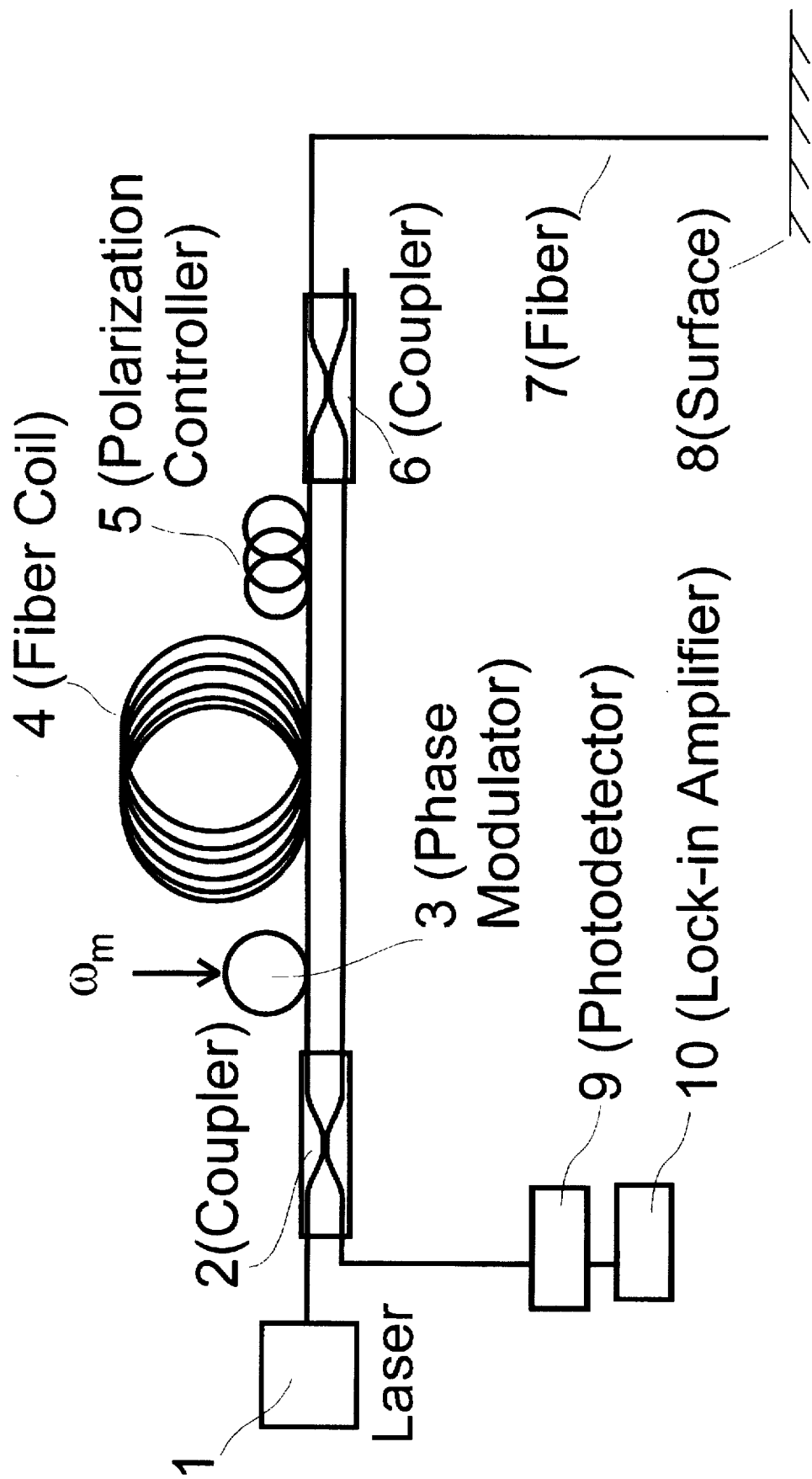
FIG. 6 – PRIOR ART

METHOD AND APPARATUS FOR DETECTION OF ULTRASOUND USING A FIBER-OPTIC INTERFEROMETER

The invention relates generally to a method and apparatus for the optical detection of transient motion in an object, and more specifically to the noncontact detection of ultrasound during nondestructive testing.

BACKGROUND OF THE INVENTION

The generation and detection of ultrasonic acoustic waves is widely used for imaging the interior of solid objects in nondestructive testing and evaluation (NDE), as well as for dimension gauging and for measuring material properties such as elastic constants. The most common devices used for generation and detection of ultrasound are piezoelectric transducers, which typically have very high sensitivity. These transducers require direct contact with the object being tested or indirect contact through a liquid column or a solid wedge. However, in many applications completely noncontact ultrasonic inspection, where there is no physical contact, either directly or indirectly, with the object being tested, is desirable. Examples include inspection of objects which are at high temperature, objects with curved surfaces, objects sensitive to contamination, or where conditions require that fast scans be preformed.

Ultrasonic inspection can be performed without direct or indirect physical contact using a pulsed laser that generates ultrasound at the surface of the object to be inspected, which then propagates to the object's interior, in combination with optical interferometric apparatus and methods that detect the very small undulations created by reflected waves reaching the surface of the object. This technique is generally called laser-ultrasonics (LUT) or laser-based-ultrasound (LBU). A description of several applications of LUT can be found in "Nondestructive evaluation with laser ultrasound," *Mechanical Engineering*, Vol. 116, p.63, 1994. However, because of the small amplitude of typical ultrasonic displacements compared to the light wavelength, optical detection remains a challenge. Thus, various techniques have been investigated and developed for optical detection of ultrasound, as described, for example, by J. P. Monchalin, "Optical detection of ultrasound," *IEEE Transactions on Ultrasonics, Ferroelectrics, and Frequency Control*, Vol. UFFC-33, p. 485, 1986, and by J. W. Wagner, "Breaking the sensitivity barrier: the challenge for laser ultrasonics," *IEEE Ultrasonics Symposium*, 1051–0117/92, p. 791, 1992.

Laser-ultrasonics instrumentation for use in the field requires an interferometric system that is lightweight, compact, and environmentally rugged. Conventional interferometers do not possess these characteristics because they require the exact alignment of optical components on a rigid and heavy optical bench. Assembling the interferometer with optical fibers eliminates optical alignment problems and the need of an optical bench. However, perturbations such as temperature changes and vibrations cause a substantial change of the fiber delay and consequently most fiber-optic interferometers are adversely susceptible to perturbations of this type.

The J. E. Bowers and G. S. Kino, U.S. Pat. No. 4,572,949, Feb. 25, 1986, discloses prior art of a fiber-optic ultrasonic detector that avoids the problems caused by temperature changes and vibrations by using a configuration known in the art as a Sagnac interferometer. A detailed explanation of its working principle is also found in the corresponding patent document. FIG. 6, adapted from the referred patent, shows this prior art. Unfortunately, in the Sagnac interferometer, one-half of the light reaching the detector does not convey a signal useful for detecting desired information, and therefore, that light increases the background noise and limits the instrument sensitivity. Moreover, the response obtained by the Sagnac interferometer is proportional to the square of the ultrasonic signal amplitude, which is very small, unless a phase modulator is inserted inside the loop. Inserting the phase modulator creates harmonic distortion and consumes electrical power, and in addition the modulator is expensive. An alternative embodiment disclosed in the referred patent is to use a polarization controller inside the Sagnac loop and take advantage of the fiber residual birefringence, but with this approach the advantages of environmental insensitivity are lost because the interferometer is sensitive to perturbations to the fiber birefringence.

SUMMARY OF THE INVENTION

It is a purpose of this invention to disclose a device for laser detection of ultrasound using a fiber-optic interferometer that is environmentally rugged and particularly advantageous for use in the field. Elements of this invention were disclosed at two conferences: J. Alcoz, "Stable fiber-optic interferometer for ultrasonic detection using passive components," 1996 *Optical Society of America Annual Meeting* (Paper TuQQ52), Oct. 22, 1996, and in J. Alcoz, C. Duffer, and S. Nair, "Noncontact detection of ultrasound with rugged fiber-optic interferometer," *IEES 1996 Ultrasonic Symposium* (Paper B-3), Nov. 4, 1996.

The prior art in optical detection of ultrasound using fiber-optic interferometers requires the use of one or more of the following components as described, for example, in the cited review paper by Monclialin: (1) temperature-stabilized high-coherence lasers (e.g., long-path-difference interferometers), (2) electronic feedback with fiber stretchers or other optical-path correction (e.g., stabilized Michelson and Mach-Zendlier interferometers), and (3) optical frequency or phase modulation (e.g., heterodyne interferometers or the previously mentioned Bowers' patent). In contrast, the present invention does not require any of these components or methods. In particular, the fiber-optic interferometer in the present invention remains passively locked at its more sensitive operating point under wide temperature variations inside the interferometer enclosure.

The present invention consists of a path-matched interferometer of the Sagnac class. Light from a laser diode, or another monochromatic source of arbitrary coherence, simultaneously travels both clockwise and counterclockwise along an optical loop which includes the path of the light illuminating the object being inspected, reflecting from that object and then collected and coupled into the fiber. Means are provided to assure that all the light reaching the detectors has completed the closed-circuit Sagnac loop. Means are also provided to passively control the polarization and phase of the light in the interferometer. The output light is detected by two photodetectors working in a differential mode. Ultrasonic vibrations from the object being inspected modulate the amplitude of the detected signal.

The invention should not be viewed as restricted to sensing ultrasonic vibrations on a surface without contacting the surface. It should be obvious that the invention can be readily used on contact with the surface of the object being inspected. It can also be readily used by embedding the illuminating fiber in the object being inspected.

For the purposes of this disclosure, the phrase "illuminating the object" refers to any means of directing light to the object where transient motion is sensed. In the same manner, "reflected light" refers to any light that propagates backwards from the object being inspected towards the sensing apparatus, regardless of the physical origin of backscatter.

In its preferred embodiment, light from a laser diode is coupled with a fiber directional coupler into two polarization-maintaining (PM) optical fibers. Polarized light propagating along the slow mode in one fiber is coupled by a polarizing beam-splitter into the slow mode of a third PM fiber. A fiber polarization controller converts this mode into right circular polarization that is focused with optical lenses on the monitored area of the object being investigated. Part of the reflected or scattered light is collected by the lens and coupled to the fiber, and the polarization controller converts this light into the fast polarization mode. The polarizing beam-splitter directs this light to the second PM fiber, and the light returns to the first directional coupler after completing the optical loop in the clockwise direction. Likewise, light originally coupled to the fast mode of the second fiber travels counterclockwise along the identical optical path.

A polarizing beamsplitter with its axes at 45 degrees with respect to the axes of the loop fibers is used to combine the clockwise and counterclockwise beams of light and to obtain two interference signals. Because one fiber arm of the loop is much longer than the second fiber arm, the area of the object being inspected is at an asymmetrical location with respect to the loop center and ultrasonic displacements will generate transient phase differences between the counter-propagating beams. The static phase difference between these light beams is fixed at 90 degrees by the phase-retardation produced by a polarization controller at the input or output of the Sagnac loop. The two interference signals are amplitude modulated by the ultrasound but are 180 degrees out of phase. They are subtracted electronically to double the desired ultrasonic signal while most noise sources, such as intensity noise of the laser, are canceled.

Perturbations to the optical path, due for example to temperature changes or mechanical vibrations, equally affect light propagating in both directions in the path, as long as the perturbations are slow compared with the transit time of the loop. Thus, they do not produce an output signal, nor do they change the operating point of the interferometer. This is a consequence of the perfect optical-path-match between the clockwise and counterclockwise propagating light. It is pointed out that, although the beams change their polarization state several times while traveling along the optical path, at each specific point in this closed-circuit path the polarization states of the counter-propagating modes coincide.

BRIEF DESCRIPTION OF THE DRAWINGS

The invention will be described in further detail with reference to the accompanying drawings, in which:

FIG. 6 is a prior art schematic diagram of an ultrasonic detector using a fiber-optic Sagnac interferometer.

DETAILED DESCRIPTION OF THE INVENTION

Figure 2:
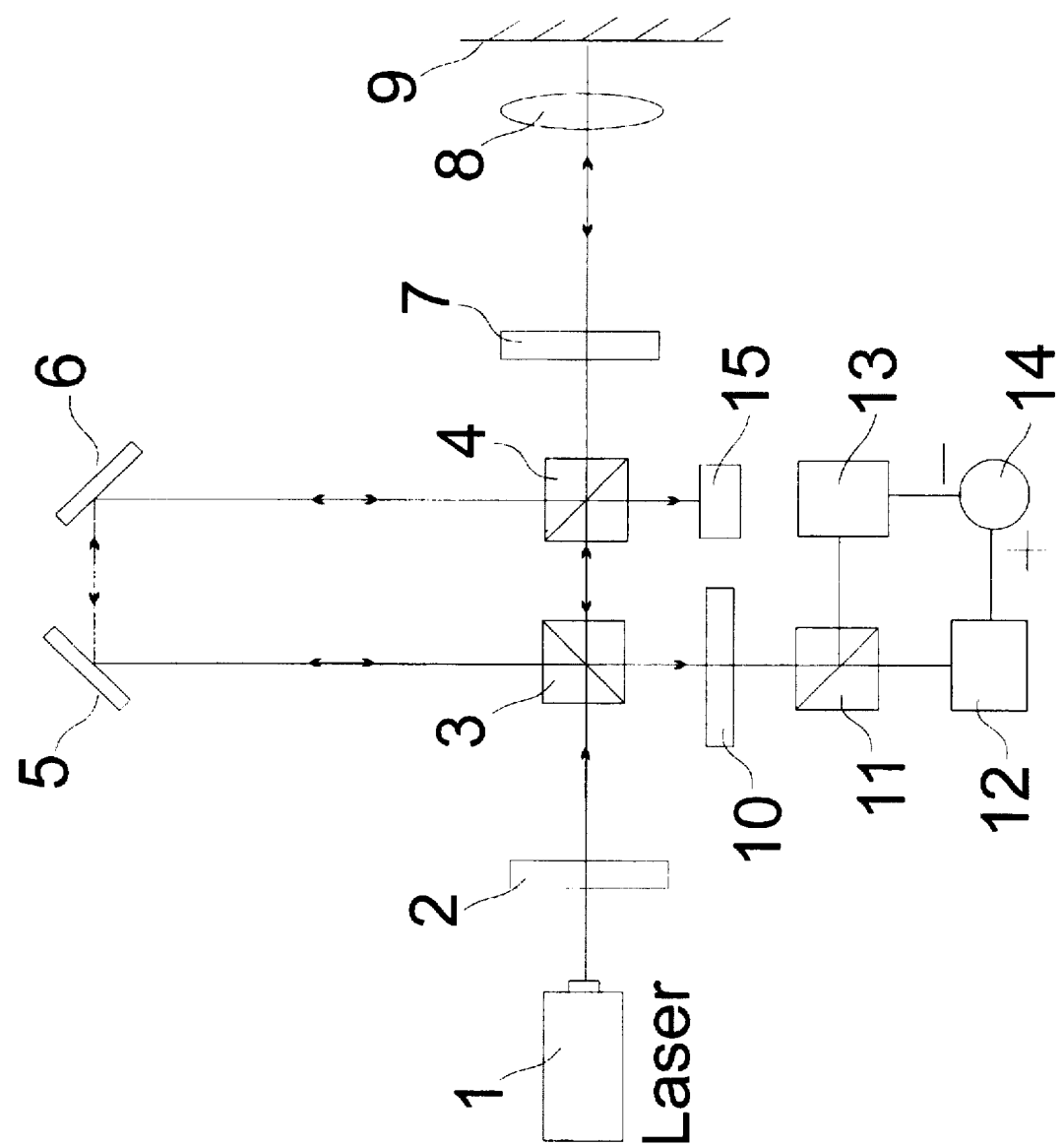
FIG. 2 is a schematic diagram of an embodiment of the ultrasonic detector utilizing discrete optical components.

The principle of ultrasonic detection utilizing an optical bench is first described in reference to FIG. 2. This embodiment, operating at ultrasonic frequencies higher than those normally used in industrial NDE, is used to clarify the explanation of its operation. The reason it is not practical for use in industrial NDE is that a very long optical path (greater than 10 meters) is required at these ultrasonic frequencies. The operational details of using optical fiber are described later in a preferred embodiment.

The light from a linearly polarized laser 1 is converted to circular polarization by a quarter-waveplate 2. The light components polarized vertically and horizontally are 90 degrees out of phase. A 50/50 non-polarizing beam-splitter 3 splits the light into two equal-power beams, the clockwise (c.w.) beam traveling towards the mirror 5 and the counter-clockwise (c.c.w.) beam traveling towards the polarizing beam-splitter 4. The c.w. beam is reflected by mirrors 5 and 6, which serve as an optical delay, and reaches the polarizing beam-splitter 4. The horizontally polarized component of the c.w. beam is transmitted towards a light dump 15 while the vertically polarized component is reflected towards a second quarter-waveplate 7. The quarter-waveplate 7 has its axes rotated 45 degrees with respect to the c.w. beam and converts this vertically polarized light into right circular polarized light. This light beam is focused by a lens 8 on the ultrasonically vibrating surface 9.

The reflected or scattered beam from surface 9 is left circular polarized and part of it is collected by lens 8. This collected light is converted by the quarter-waveplate 7 to horizontally polarized light which is transmitted by the polarizing beam-splitter 4, without any light being reflected towards mirror 6, completing the clockwise path of the loop.

In like manner, the vertical component of the c.c.w. beam propagating from the non-polarizing beam-splitter 3 towards the polarizing beam-splitter 4 is reflected towards the light dump 15 by the polarizing beam-splitter 4, and the horizontally polarized beam is transmitted towards the quarter-waveplate 7 which converts the polarization of this light to left circular polarized light. This beam is focused by lens 8 on the ultrasonically vibrating surface; it is reflected by the surface as right circular polarized light; and finally it is converted to vertical polarized light by waveplate 7. All of this beam is reflected by the polarizing beam-splitter 4 and completes the c.c.w. path 6-5-3. It should be noted that the path between beam-splitter 4 and the surface 9 is part of the Sagnac loop, even though it is a linear path. This is so because light travels towards the surface with polarization which is orthogonal to the polarization it has upon returning from the surface, and the c.c.w. light changes polarization modes in reverse order to that of the c.w. light.

One-half of the power of the vertically polarized c.w. and the horizontally polarized c.c.w. beams are sent towards a compensating waveplate 10 by the non-polarizing beam-splitter 3. The purpose of waveplate 10 is described in the following paragraphs. A second polarizing beam-splitter 11 at 45 degrees with respect to the c.w. and c.c.w. polarization axes combines these two vertically and horizontally polarized beams producing two new beams traveling towards photodetector devices 12 and 13. These beams are the result of the interference of the counter-propagating modes, and thus their amplitudes are modulated by the phase difference between the interfering modes. This is well known in the art of interferometry. In the absence of an ultrasonic signal, the c.w. and c.c.w. beams travel exactly the same optical path inside the loop, without any relative phase shift being introduced between them. However, the first quarter-waveplate 2 introduces outside the loop a 90 degrees static bias between the two beams which is present until they interfere at the polarizing beam-splitter 11. The output of the interferometer is a (vertically shifted) cosine function of this phase difference, as in every single-path interferometer. Thus, the 90 degrees static bias assures that the operating point of the interferometer is fixed at the linear part of the response curve. In the presence of ultrasonic vibrations, the surface 9 of the object being inspected will move in the time increment between which it is reached by the c.c.w. beam traveling first through the short arm 3-4-7-8-9 and the corresponding portion of the c.w. beam traveling first through the long arm 3-5-6-4-7-8-9. This will produce a dynamic phase shift between the two interfering beams. When the time delay difference between these beams traveling in the short and long arms is equal to half the period of the ultrasonic center frequency, or an odd multiple of it, one beam will see a peak of the wave when the corresponding portion of the other beam sees a valley, producing the largest relative phase modulation.

In addition to the 90 degrees static phase-shift provided by the first waveplate 2, the only other possible sources of static phase difference are spurious birefringence retardation at the input and output glass of beam-splitter 3 or the input glass of beam-splitter 11. These non-desired shifts are compensated by a phase-retardation waveplate 10. Alternatively, the 2 and 10 waveplates can be interchanged in their positions or be placed together either at the output or at the input of the loop.

The output signal can be doubled and, at the same time, the contribution of noise can be greatly diminished, by using a balanced detector. This takes advantage of the fact that the outputs detected by the photodetectors are complementary, i.e., when the power reaching the first detector increases due to a change in phase difference, the power reclining the second detector decreases. Balanced detectors are widely used in sensors based on the interference of orthogonal polarizations. In this embodiment the outputs of the photodetectors are subtracted electronically at 14 to obtain the desired signal.

Figure 1:
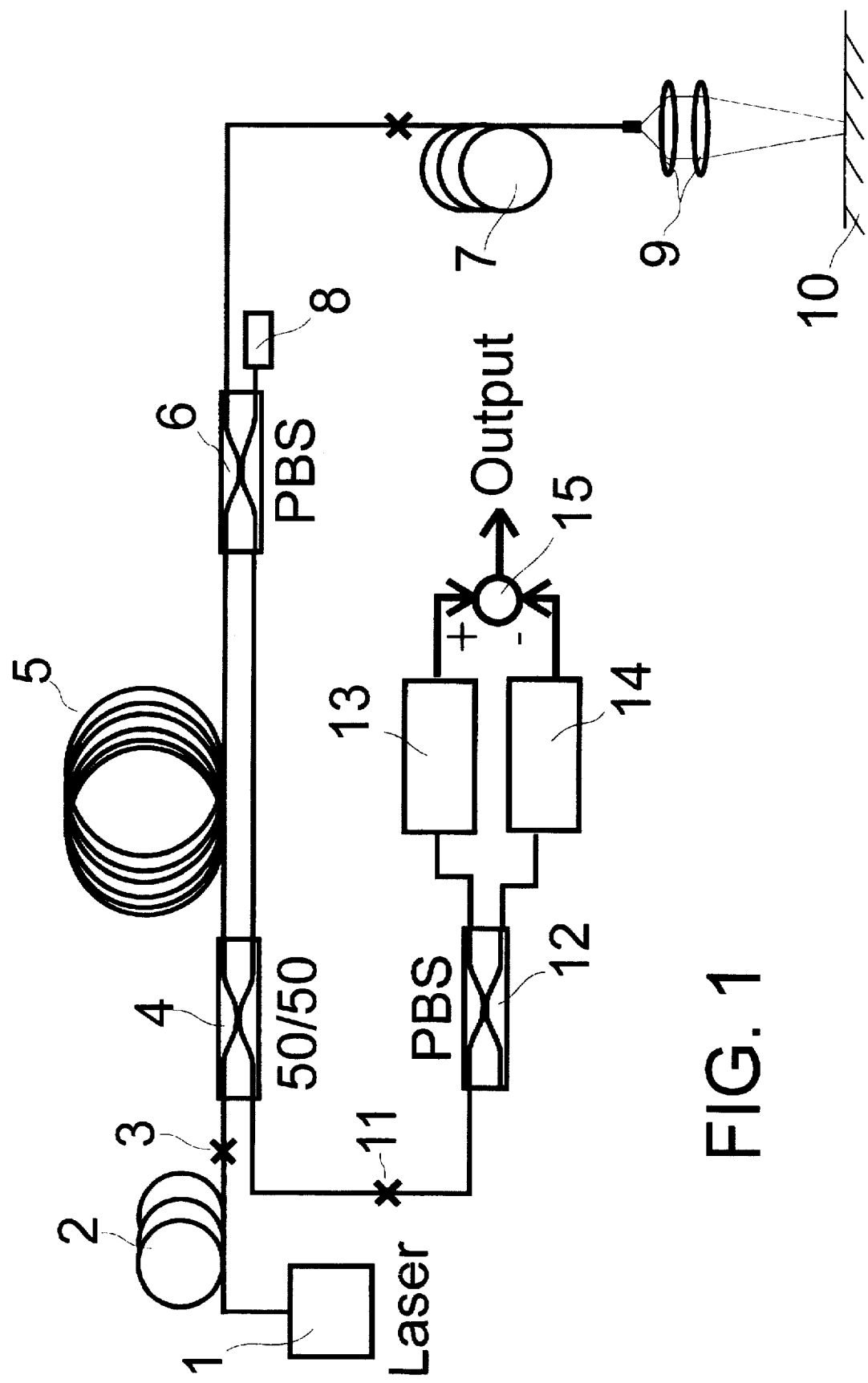
FIG. 1 is a schematic diagram of a preferred embodiment of the ultrasonic detector utilizing PM optical fibers.

The preferred embodiment of the invention is shown in FIG. 1. The embodiment disclosed in FIG. 1 and discussed in detail presents an advantage with respect to the embodiment of FIG. 2.

In the embodiment shown in FIG. 1 light is guided by optical fibers and no alignment of discrete components on an optical bench is necessary. Furthermore, the long optical delay needed in one arm of the loop is achieved by a compact coil of fiber.

The light from a laser diode 1 is coupled to a single mode fiber. A fiber-polarization-controller (FPC) 2 is used to adjust the polarization of the light injected at point 3 to the input polarization-maintaining (PM) fiber of the interferometer. PM fiber has two possible modes of propagation with polarized light aligned along orthogonal axes. These modes are a slow and a fast propagating mode. This is a result of birefringence introduced during manufacture. A 50/50 PM fiber directional-coupler 4 splits the light from the laser diode 1 into two equal power c.w. and c.c.w. beams. The c.w. light travels through a long length of PM fiber 5, which results in a time delay, before reaching the fiber polarizing-beam-splitter (PBS) 6. The c.w. light propagating along the fast mode of the PM fiber 5 is coupled towards a light dump 8, while the c.w. light polarized along the slow mode is transmitted towards a second FPC 7. The c.w. light transmitted towards FPC 7 is focused by a lens assembly 9 on the surface 10 of the object being inspected where ultrasonic waves are present. Part of the reflected or backscattered light is collected by the lens assembly 9 and coupled back into the fiber. The FPC 7 is adjusted so that it works as a quarter-waveplate, thus converting the c.w. linearly-polarized light (slow-mode) into right-circular polarized light at its output and the collected left-circular polarized light into light polarized along the PM fiber fast-mode. The PBS 6 directs all of this light to the short arm of the loop, and it reaches the directional coupler 4, completing the remaining portion of the c.w. path.

In like manner, light coupled by fiber-directional-coupler 4 to the short arm of the loop is split at PBS 6 into the slow mode which is directed towards the light dump 8, and the fast mode that travels towards the FPC 7, which converts it to left-circular polarized light, and is focused by the lens 9 onto the surface 10 of the object being inspected. Part of the reflected or backscattered light is collected by lens 9 and coupled back into the fiber. The FPC 7 converts the collected c.c.w. light, which is right-circular polarized, into light linearly polarized along the slow-mode of the PM fiber. The PBS 6 couples all of the c.c.w. light towards the long arm of the loop. The c.c.w. light is delayed by the long PM fiber arm 5 and reaches the directional-coupler 4, completing the remaining portion of the c.c.w path of the loop.

One-half of the c.w. and c.c.w propagating light is coupled by the directional coupler 4 into the output PM fiber 4-11. This fiber is connected at splice point 11 to the input PM fiber of a second fiber polarizing-beam-splitter PBS 12. The axes at splice point 11 of the two PM fibers are rotated 45 degrees with respect to each other. Thus, the c.w. and c.c.w. modes interfere at this point producing two orthogonally polarized modes that are separated by PBS 12 and detected by photodetectors 13 and 14. The resulting interference signals are complementary and are electronically subtracted at 15 to obtain a signal modulated by the ultrasound present at the surface of the object being inspected.

The FPC 2 is adjusted so that equal power is coupled at input point 3 to the slow and fast modes and so that the static phase difference between the modes when they interfere at splice point 11 is 90 degrees. In general, when this condition is obtained, the light coupled at point 3 will not be circularly polarized, i.e. the fast and slow modes generated will not have a phase difference of 90 degrees. The input and output to the Sagnac loop introduce phase-shifts, because the PM fiber lengths to the left of 4 (i.e., 3-4 and 4-11) are not part of the path-matched Sagnac loop.

This is a disadvantage with respect to the embodiment of FIG. 1 because the fiber lengths outside the proper Sagnac loop are sensitive to environmental perturbations and to frequency variations of the laser. The environmental perturbations are minimized by making the length of these fibers as short as possible. The effect produced by frequency variation is minimized if the two fiber lengths are of the same type of fiber and of the same length. The reason is that light propagating in the slow mode at the input fiber will propagate in the fast mode at the output fiber and vice versa. Thus, variations in the beat-length between the modes, due to changes in laser frequency, are canceled if the fibers are of identical length.

Figure 3:
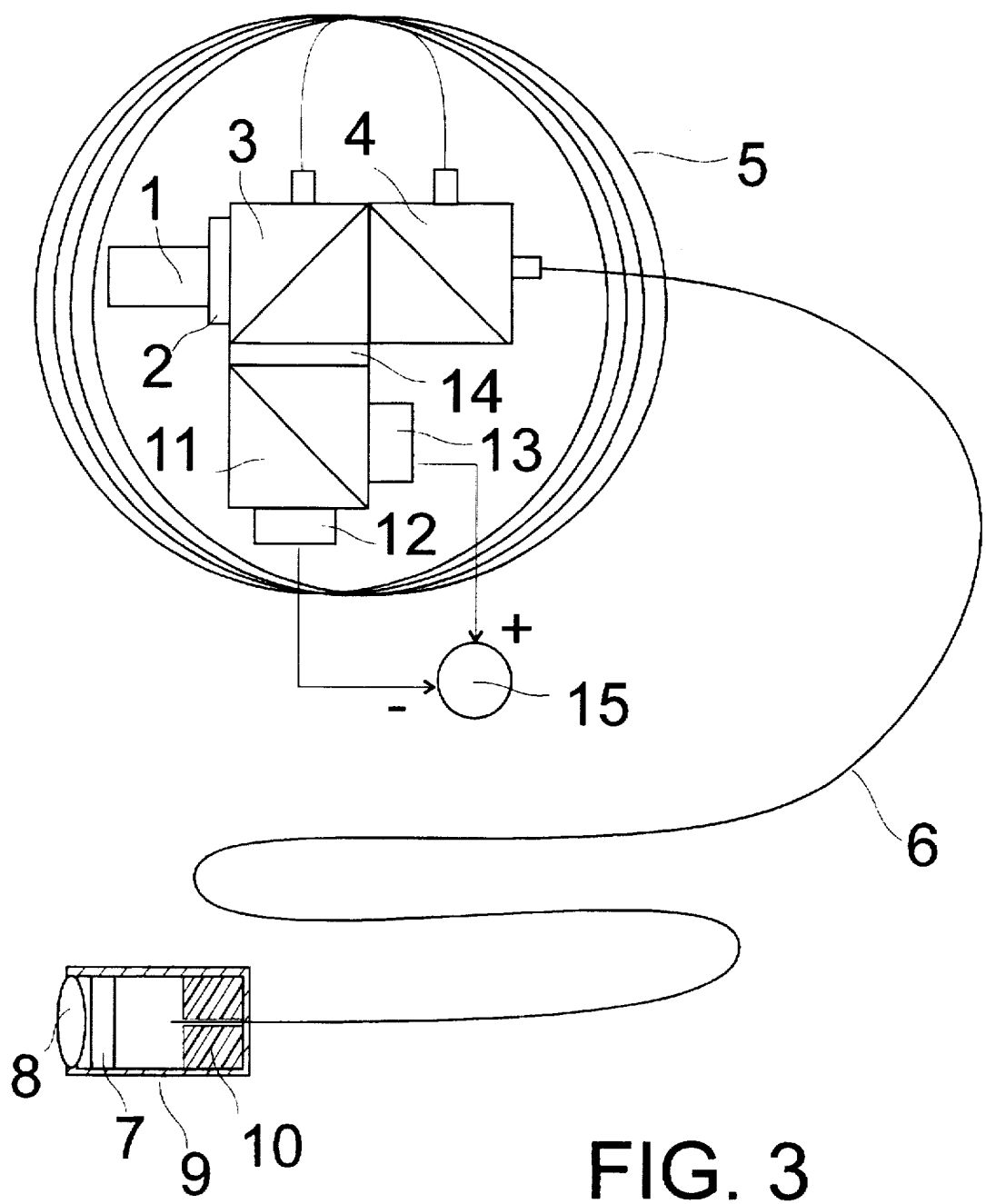
FIG. 3 is a schematic diagram of an alternative embodiment of the ultrasonic detector using a combination of discrete optical components and PM optical fibers.

FIG. 3 shows an alternative embodiment of the invention. This embodiment combines discrete optical components with PM optical fiber parts, therefore being a hybrid between the embodiments disclosed in FIG. 1 and FIG. 2. The operating principle is similar to the one described in relation to FIG. 1 since the components of this embodiment are: laser diode 1, quarter-waveplate 2, 50/50 beam-splitter 3, PBS 4, PM fiber 5, PM fiber 6, quarter-waveplate 7, focusing lens 8, probe case 9, fiber holder 10, PBS 11, photodetectors 12-13, compensating waveplate 14, and electronic subtraction circuit 15. The waveplate 2 converts the light from the laser 1 into circular polarized light, which is split by beam-splitter 3 and directed into the c.w. and c.c.w. paths. The PBS 4 sends one polarization mode of each path along the PM fiber 6 towards the probe 9. The waveplate 7 in the probe converts each mode to circular polarized light and light reflected from the surface of the object being inspected is converted by waveplate 7 back to the orthogonal mode. The output PBS 11, with its axes at 45 degrees with respect to the fiber, produces the two interference beams which are detected by the photodetectors 12 and 13, and thereafter are subtracted electronically at 15. Waveplate 14 compensates for spurious birefringence as described in relation to FIG. 2 and can also be used to rotate the c.w. and c.c.w. polarization axes 45 degrees without physically rotating PBS 11.

Figure 4:
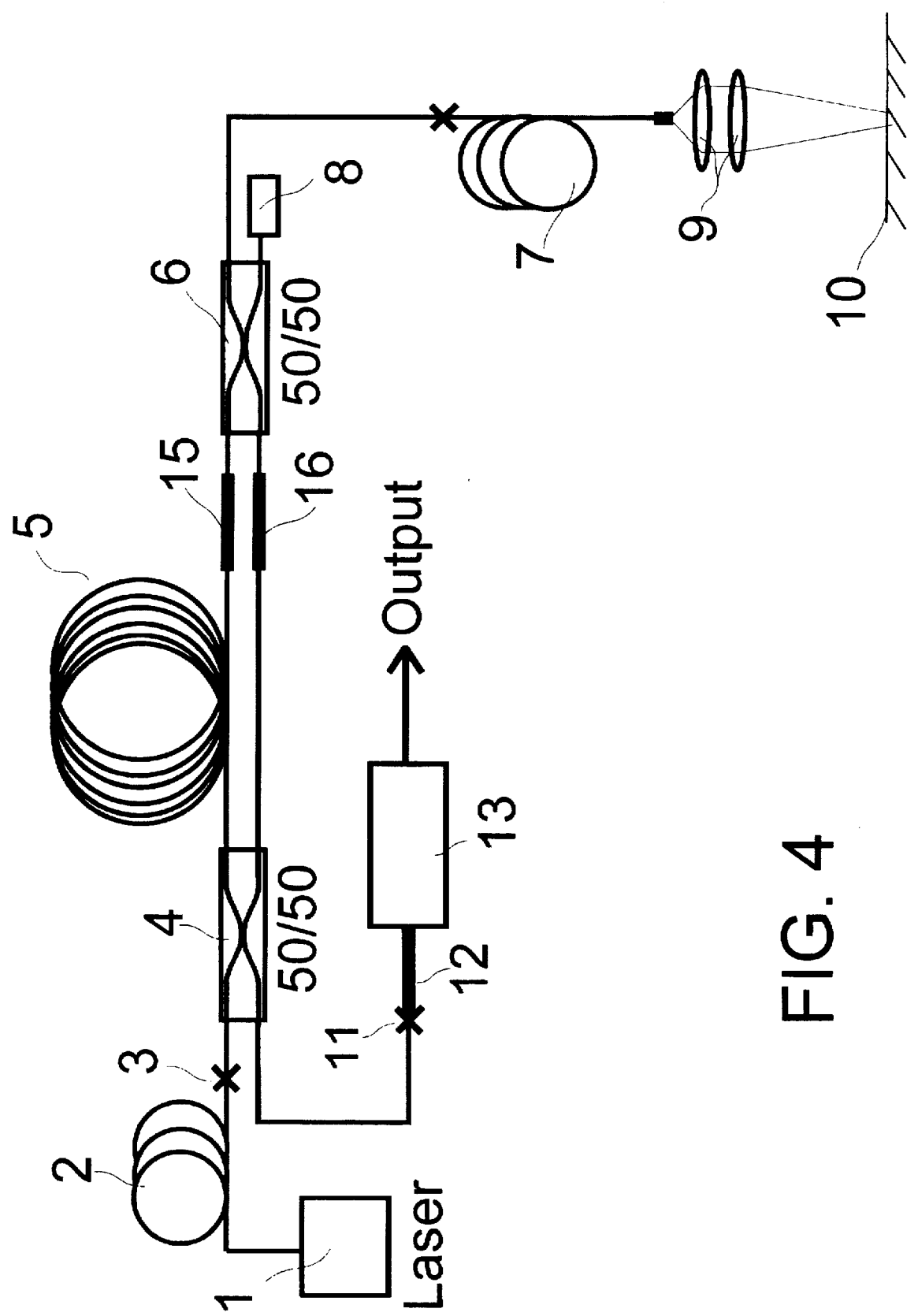
FIG. 4 is a schematic diagram of an alternative embodiment of the ultrasonic detector that does not use polarizing beam-splitters.

FIG. 4 shows another embodiment of this invention. This embodiment is similar to the embodiment disclosed in FIG. 1, except that the polarizing beam-splitter in FIG. 1 is replaced by a PM directional coupler 6 as shown in FIG. 4, and two lengths of polarizing fiber 15 and 16 are inserted in the Sagnac loop. The rest of the components are identical to those disclosed in FIG. 1. Polarizing (PZ) fiber only supports the propagation of a single polarization mode, contrary to the effect of PM fiber, consequently it polarizes light coupled at its input, as described by M. J. Messerly, R. C. Mikkelson, and J. R.. Onstott, "A broadband single polarization optical fiber," *Journal of Lightwave Technology*, Vol. 9, 1991. PZ fiber is employed in this embodiment to eliminate light that propagates backwards in the PZ fiber without having traversed the complete Sagnac loop. The light from a laser diode 1 is coupled to FPC 2 which is used to adjust the polarization of the light injected at point 3 to the input PM fiber of the interferometer, as explained in relation to the embodiment of FIG. 1. A 50/50 PM fiber directional-coupler 4 splits the light into two equal power c.w. and c.c.w. beams. The c.w. propagating light travels through a long length of PM fiber 5, which results in a time delay, and through a length of PZ fiber 15. This eliminates the linearly polarized fast mode. One-half of the light propagating along the slow mode of the fiber is coupled towards a light dump 8, while the other half travels towards FPC 7 adjusted as a quarter-waveplate. The c.w. output light from FPC 7, which is right-circularly polarized light, is focused by a lens assembly 9 on the surface of the object being inspected where ultrasonic waves are present. Part of the reflected or backscattered light is collected by the lens assembly 9 and is coupled back to the fast mode of the PM fiber. The 50/50 PM directional-coupler 6 directs one-half of this light to the short arm of the loop. The other half is coupled into the long arm and eliminated by the PZ fiber 15, because the propagation axis of the PZ fiber is aligned with the slow mode. However, the PZ fiber 16 has its propagation axis aligned with the fast mode of the short arm, and the light can complete the c.w. path. In the same manner, c.c.w. propagating light coupled by directional coupler 4 to the short arm becomes polarized by the PZ fiber 16 along the fast mode and one-half of the light is coupled at directional coupler 6 into the fast mode of the third arm. This c.c.w. light travels towards the surface of the object being inspected and part of the reflected or backscattered light collected by lens 9 is completed into the fiber and traverses the complete c.c.w. path polarized along the slow mode of the long arm. The fiber carrying the light from directional coupler 4 is spliced at point 11 to a PZ fiber 12 with its axes rotated 45 degrees, so as to produce an interference signal that is detected by a photodetector 13. This embodiment has the advantage of not requiring a polarizing beam-splitter, but is not very efficient in its use of light power.

Figure 5:
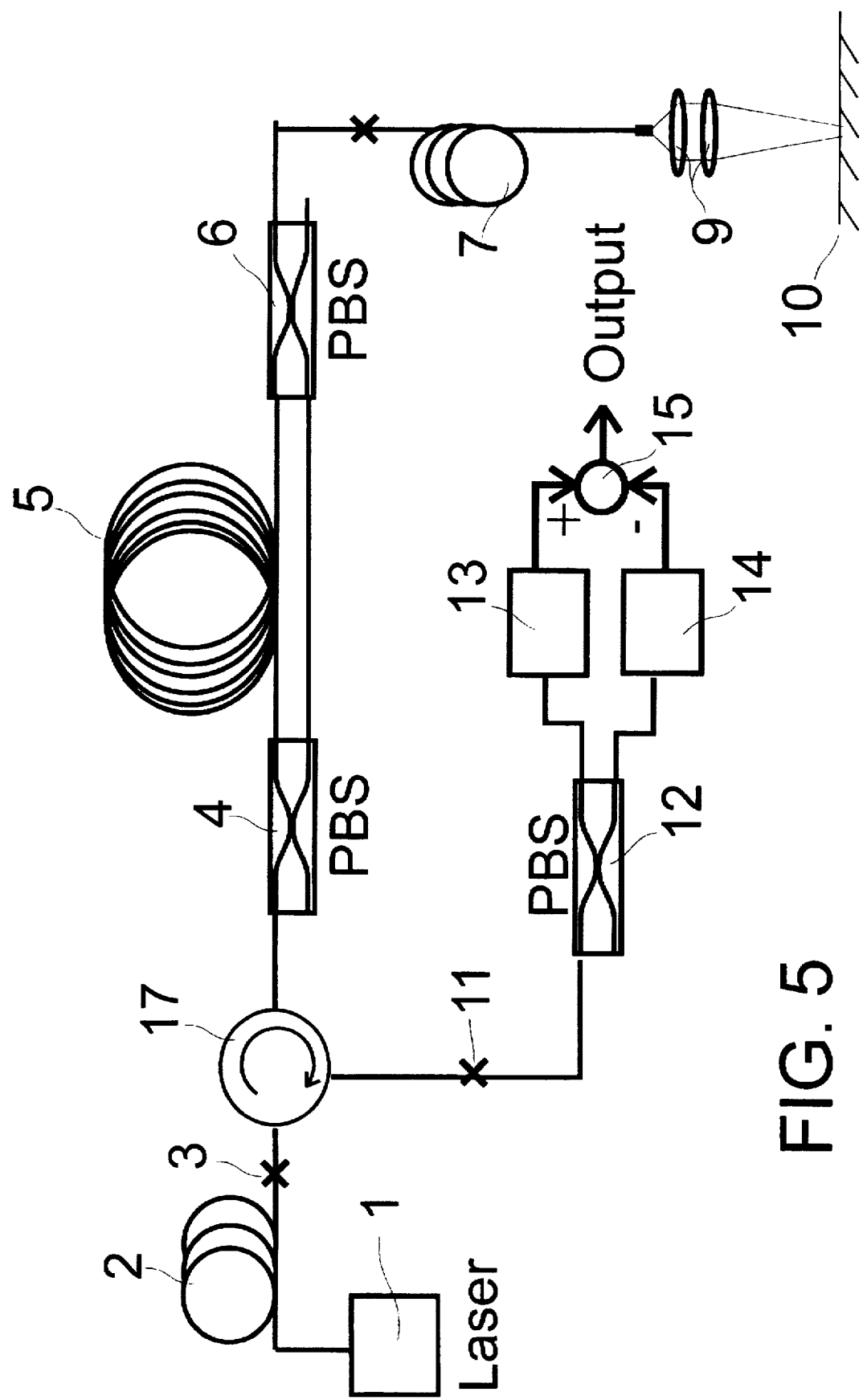
FIG. 5 is a schematic diagram of an alternative embodiment of the ultrasonic detector having increased efficiency in its use of light.

FIG. 5 shows yet another embodiment of this invention. This embodiment is similar to that disclosed in FIG. 1, except that the input 50/50 directional-coupler 4 is replaced by a polarizing beam-splitter 4 and an optical circulator 17 is added. This embodiment has the advantage of increased efficiency because no light is lost as a result of dumping to unused ports. The light from a laser diode 1 is coupled to FPC 2 which is used to adjust the polarization of the light injected at point 3 to the input PM fiber of the interferometer. An optical circulator 17 built with PM fiber transmits all the light towards PBS 4. Fiber optical circulators are described, for example, by Jay Van Delden, "A new approach to fiber coupling" *Photonics Spectra*, January 1992. PBS 4 splits the light into a component polarized along the slow mode and traveling c.w., and a component polarized along the fast mode and traveling c.c.w. The c.w. light travels through a long length of PM fiber 5, which results in a time delay, and reaches the fiber-polarization-splitter 6. All the c.w. light is transmitted towards FPC 7, adjusted as a quarter-waveplate. This light from FPC 7 is focused by a lens assembly 9 on the surface where ultrasonic waves are present. Part of the reflected or backscattered light is collected by lens 9 and is coupled back into the fiber. PBS 6 directs all of this light to the short arm of the loop, polarized along the fast mode. In like manner, all of the light coupled by PBS 4 to the short arm travels towards the FPC 7 and the light from FPC 7 is focused by lens assembly 9 on the surface of the object being inspected. Part of the reflected or backscattered light is collected by lens 9 and is coupled to the long arm, polarized along the slow mode. The c.w. and c.c.w. components are both completely transmitted by PBS 4 towards the optical circulator 17 which sends these beams traveling towards port 11 to interfere and be detected by differential detector 13-14-15 as explained in the discussion of the operation of the embodiment shown in FIG. 1.

It should be further realized that numerous other embodiments may be considered without departing from the scope of the invention.

What is claimed is:

1. An apparatus for detecting transient motion in an object comprising: a light source; a closed-circuit optical path comprising first and second arms of different optical-path-length that couple into orthogonal polarization modes of a third arm of said closed circuit optical path; means for splitting light from said light source into light propagating in opposite directions along said closed-circuit optical path; means for illuminating said object with light from said third arm and collecting and coupling back to said third arm reflected light from said object; means for directing said collected and coupled light traversing in opposite directions along said closed-circuit optical path such that it traverses the remaining portion of said closed-circuit optical path; means for controlling static phase difference between said collected and coupled light traveling in opposite directions along said closed-circuit optical path; means for producing an interference signal from said collected and coupled light traveling in opposite directions on said closed-circuit optical path; means for detecting said interference signal.

2. An apparatus as defined in claim 1 further comprising means for impeding said collected and coupled light from propagating a second time along the portion of said closed-circuit optical path first traversed by said collected and coupled light.

3. An apparatus as defined in claim 1 wherein said first and second arms of said closed-circuit optical path provide an optical-path difference equal in time to an odd multiple of half the period of the center frequency of sensed motion in said object.

4. An apparatus as defined in claim 1 wherein said closed-circuit optical path is determined by a non-polarizing beam-splitter, mirrors, a polarization splitter, a quarter-waveplate, and a focusing lens assembly.

5. An apparatus as defined in claim 1 wherein the said means for controlling static phase difference is comprised of a polarization controller located outside said closed-circuit optical path.

6. An apparatus as defined in claim 1 wherein said closed-circuit optical path is determined by a polarization-maintaining directional coupler, two polarization-maintaining fibers of different length comprising first and second arms of said closed-circuit optical path, a fiber polarization splitter, a third polarization-maintaining fiber comprising a third arm of said closed-circuit optical path, a polarization controller, and a focusing lens assembly.

7. An apparatus as defined in claim 1 wherein said closed-circuit optical path is determined by a polarization-maintaining directional coupler, two polarization maintaining fibers of different length comprising first and second arms of said closed-circuit optical path, two polarizing fibers of the same length, a second polarization-maintaining directional coupler, a length of polarization-maintaining fiber comprising a third arm of said closed-circuit optical path, a polarization controller, and a focusing lens assembly.

8. An apparatus as defined in claim 1 wherein the said closed-circuit optical path is determined by an optical circulator, a polarizing beam-splitter, two polarization-maintaining fibers of different length comprising first and second arms of said closed circuit optical path, a second polarizing beam splitter, a length of polarization-maintaining fiber comprising a third arm of said closed-circuit optical path, a polarization controller, and a focusing lens assembly.

9. An apparatus as defined in claim 1 wherein said means for producing an interference signal is comprised of a polarizing device aligned at 45 degrees with respect to the polarization axes of said closed-circuit optical path.

10. An apparatus as defined in claim 1 wherein said means for producing an interference signal is comprised of a polarizing beam-splitter aligned at 45 degrees with respect to the polarization axes of said closed-circuit optical path.

11. An apparatus as defined in claim 1 wherein said interference signal is proporational to the displacement amplitude of a narrow band ultrasonic signal present in said object.

12. A method of sensing transient motion in an object comprising the steps of:

splitting a light source into light propagating in opposite directions on a closed-circuit optical path;

directing said light into a first arm and a second arm of different optical path length such that said arms couple said light into orthogonal polarization modes in a third arm;

directing said light from said third arm such that it illuminates said object being inspected, collecting and coupling back into said third arm light reflected from said object resulting from illuminating said object with said light;

directing said collected and coupled light such that it traverses the remaining portion of said closed-circuit optical path;

controlling static phase difference between said collected and coupled light traversing in opposite directions along said closed-circuit optical path;

producing an interference signal from said collected and coupled light traversing in opposite directions along said closed-circuit optical path;

detecting said interference signal.

13. A method of sensing transient motion as defined by claim 12 wherein splitting said light source into light propagating in opposite directions along said closed-circuit optical path is accomplished with a polarization-maintaining directional coupler.

14. A method of sensing transient motion as defined by claim 12 wherein said first, second, and third arms of said closed-circuit optical path consist of polarization-maintaining optical fibers of different length and said coupling to orthogonal polarization modes of said third arm is accomplished with a polarizing beam-splitter.

15. A method of sensing transient motion as defined by claim 12 wherein illuminating said object and collecting and coupling back into said third arm the reflected light is accomplished by a lens assembly focused on said object.

16. A method of sensing transient motion as defined by claim 12 wherein directing said reflected light such that it traverses the closed-circuit optical path is accomplished by converting the output light from said third arm into circular polarized light using a polarization controller, and using a polarizing beam-splitter to redirect said circular polarized light into the arm opposite from that arm through which such light arrived at said beam-splitter.

17. A method of sensing transient motion as defined by claim 12 wherein controlling static phase difference between light traversing in opposite directions along said closed-circuit optical path is accomplished by a polarization controller located outside said closed-circuit optical path.

18. A method of sensing transient motion as defined by claim 12 wherein producing an interference signal from said collected and coupled light traversing in opposite directions along said closed-circuit optical path is accomplished by a polarizing beam splitter with its axes forming 45 degrees with respect to the polarization axes of the closed-circuit path.

19. A method of sensing transient motion as defined by claim 18 wherein detecting said interference signal is accomplished using a photodetector at each output port of said polarizing beam-splitter and subtracting signals detected by photodetectors.

20. A method of sensing motion as defined by claim 12 wherein said interference signal is proportional to the displacement amplitude of a narrow band ultrasonic signal present in said object.

* * * * *